(12) United States Patent
O'Rourke

(10) Patent No.: US 7,442,169 B2
(45) Date of Patent: Oct. 28, 2008

(54) METHODS OF DISTINGUISHING BETWEEN VASOCONSTRICTION AND VASODILATION AS A CAUSE OF HYPOTENSION

(75) Inventor: Michael Francis O'Rourke, Darlinghurst (AU)

(73) Assignee: AtCor Medical Pty Limited, New South Wales (AU)

( * ) Notice: Subject to any disclaimer, the term of this patent is extended or adjusted under 35 U.S.C. 154(b) by 0 days.

(21) Appl. No.: 10/591,309

(22) PCT Filed: Mar. 4, 2005

(86) PCT No.: PCT/AU2005/000310

§ 371 (c)(1),
(2), (4) Date: Sep. 1, 2006

(87) PCT Pub. No.: WO2005/084535

PCT Pub. Date: Sep. 15, 2005

(65) Prior Publication Data

US 2007/0179384 A1    Aug. 2, 2007

(30) Foreign Application Priority Data

Mar. 5, 2004    (AU) ............................ 2004901160

(51) Int. Cl.
*A61B 5/02*    (2006.01)
(52) U.S. Cl. .................... 600/483; 600/481; 600/485; 600/500

(58) Field of Classification Search ................ 600/481, 600/483–486, 488, 500–504
See application file for complete search history.

(56) References Cited

U.S. PATENT DOCUMENTS

| 5,101,828 | A | * | 4/1992 | Welkowitz et al. | 600/481 |
|---|---|---|---|---|---|
| 5,265,011 | A | * | 11/1993 | O'Rourke | 600/485 |
| 6,293,915 | B1 | * | 9/2001 | Amano et al. | 600/501 |
| 6,348,038 | B1 | * | 2/2002 | Band et al. | 600/485 |
| 6,428,482 | B1 | * | 8/2002 | Sunagawa et al. | 600/485 |
| 7,192,403 | B2 | * | 3/2007 | Russell | 600/504 |
| 7,198,602 | B2 | * | 4/2007 | Eide | 600/485 |

FOREIGN PATENT DOCUMENTS

| WO | WO 90/11043 A1 | 10/1990 |
|---|---|---|
| WO | WO 96/39074 A1 | 12/1996 |

OTHER PUBLICATIONS

International Search Report, Application No. PCT/AU2005/000310 Date of Mailing: May 27, 2005.
International Preliminary Report on Patentability issued by the International Bureau of WIPO in respect of the basic U.S. Application PCT/AU2005/000310 Dated Mar. 4, 2005.

* cited by examiner

*Primary Examiner*—Charles A. Marmor, II
*Assistant Examiner*—Navin Natnithithadha
(74) *Attorney, Agent, or Firm*—Abelman, Frayne & Schwab

(57) ABSTRACT

The present invention relates to the use of the arterial pressure waveform recorded invasively or non-invasively, to distinguish between compensatory vasoconstriction with low cardiac output on the one hand from vasodilation from more severe organ damage on the other, as a cause of hypotension in acute emergencies. The waveforms may be subjected to harmonic analysis and the moduli of their harmonic components compared whereby a hypotensive individual can be confirmed to have the higher (second and above) greater than the first harmonic is considered as having vasoconstriction as a cause of hypotension.

3 Claims, 4 Drawing Sheets

NORMAL

NORMAL

HYPOTENSION WITH VASOCONSTRICTION

HYPOTENSION WITH VASODILATION

NORMAL

HYPOTENSION WITH VASOCONSTRICTION

HYPOTENSION WITH VASODILATION

METHODS OF DISTINGUISHING BETWEEN VASOCONSTRICTION AND VASODILATION AS A CAUSE OF HYPOTENSION

FIELD OF THE INVENTION

The present invention relates to the use of the arterial pressure waveform recorded invasively or non-invasively, to distinguish between compensatory vasoconstriction with low cardiac output on the one hand from vasodilation from more severe organ damage on the other, as a cause of hypotension in acute emergencies.

BACKGROUND ART

The early work of Hamilton and colleagues (Am J Physiol 1944; 141:235-41) during World War 2 showed the differences in pressure waveforms that are seen in hypotension, and how hypotension associated with vasodilation and secondary shock was associated with damped pressure waveforms and small or absent diastolic pressure fluctuations—see FIG. 1.

Subsequent work (O'Rourke M F, Am Heart J 1971; 82:687-702, Nichols and O'Rourke, McDonald's Blood Flow in Arteries; Arnold, London 1998 p. 170-189) (FIG. 2) has shown repeatedly in humans and experimental animals, that acute blood loss or fall in cardiac output from other causes is associated with amplification of the peripheral pressure wave, with prominence in the diastolic components of these waves—See FIG. 2. This was attributed to a combination of vasoconstriction, causing increased wave reflection, together with shortening of systole caused by tachycardia, such that secondary pressure waves became unusually prominent.

Further studies on frequency components of the pressure and flow waveforms confirmed these explanations and raised the possibility that automatic methods could be applied to pressure waves to distinguish uncomplicated from complicated shock through identification of change in frequency components of the pressure waves as well as from change in the secondary fluctuations of the waveforms in the time domain.

SUMMARY OF THE INVENTION

According to one aspect of the invention there is provided a method for measuring (invasively or non-invasively) the arterial pressure waveform from a peripheral artery, recording those waveforms and identifying secondary pressure waveforms.

Preferably, a series of pressure waveforms are ensemble-averaged into a single waveform to provide consistency of waveform detail. The waveforms may be subjected to harmonic analysis and the moduli of their harmonic components compared whereby a hypotensive individual can be confirmed to have the higher (second and above) greater than the first harmonic is considered as having vasoconstriction as a cause of hypotension.

Furthermore, a hypotensive individual in sinus rhythm or without significant arrhythmia is confirmed to have the lowest fundamental harmonic, at heart rate less than 120/min, dominant over all other harmonics and can be concluded as likely to have vasodilatation as the cause of hypertension.

Preferably, in the hypotensive individual, amplitude of the primary wave (peak to wave foot) is compared to amplitude of the secondary waveform (secondary peak to wave foot) and the secondary wave confirmed to have amplitude less than 25% of the initial waveform as denoting hypotension due to vasodilation whereas amplitude of the secondary waveform greater than 30% of the initial wave denotes hypotension due to vasoconstriction and acute blood loss, cardiac failure, tamponade or pulmonary embolism.

MODES FOR CARRYING OUT THE INVENTION

The present invention provides a method for determining whether hypotension in a critically ill individual is due to vasoconstriction (denoting blood or fluid loss or acute heart failure), or to vasodilation due to sepsis or organ failure.

The pressure waveform is determined accurately in a peripheral artery—preferably radial, brachial, axillary or femoral by direct puncture or by applanation tonometry or other validated method, and ensuring there is no obstruction to arteries upstream.

These pressure waveforms are recorded preferably by synchronising from a simultaneously-recorded ECG for ensemble analysis or from use of the rising limb of the pressure waveform itself.

The amplitude of the initial pressure waveform is compared with the amplitude of the secondary diastolic pressure wave in the time domain.

Figure 1:
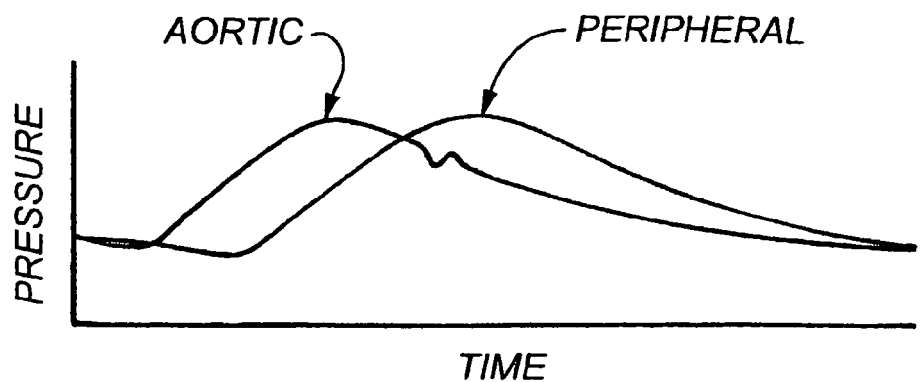
FIG. 1 shows various pressure waveforms that are seen in hypotension.
Figure 2:
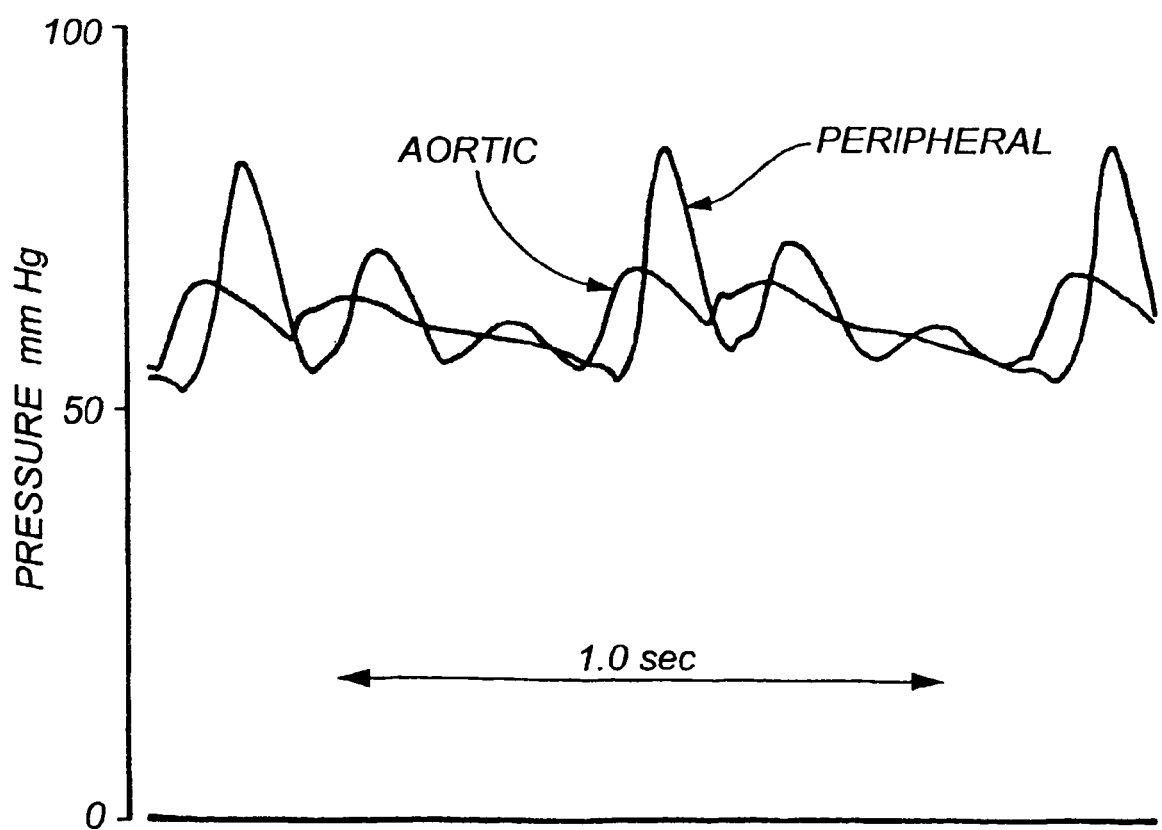
FIG. 2 shows pressure waves recorded simultaneously in the aortic arch (lower amplitude wave) and brachial artery (higher amplitude tracing) of a human with hypotension and clinical features of peripheral vasoconstriction.
Figure 3A:
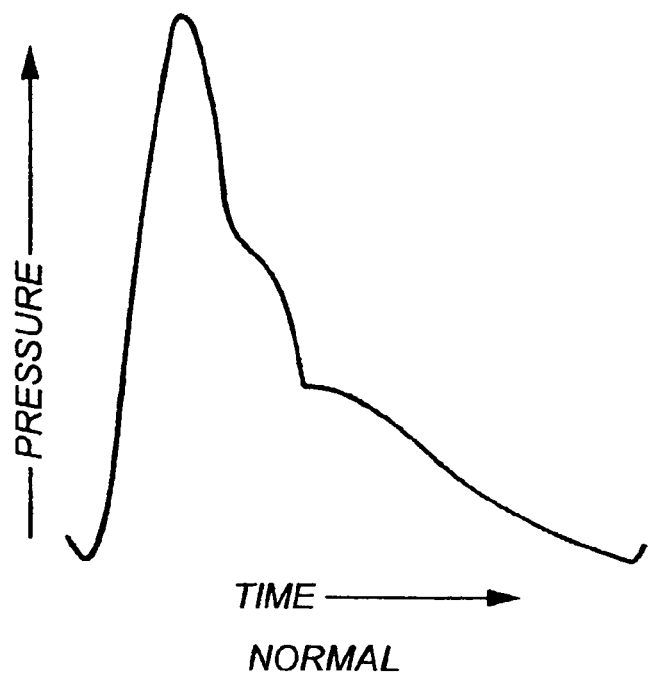
FIG. 3a shows the pressure waveform in a peripheral artery under normal conditions.
Figure 3B:
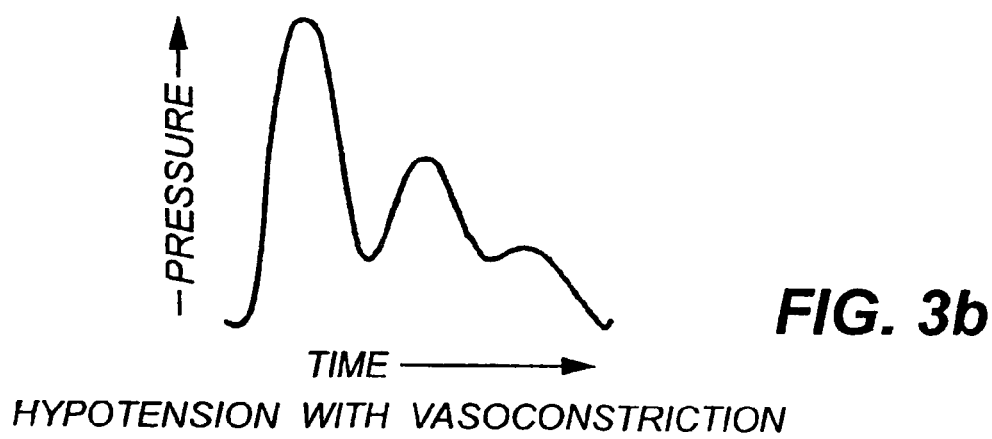
FIG. 3b shows the pressure waveform in a peripheral artery associated with vasoconstriction.
Figure 3C:
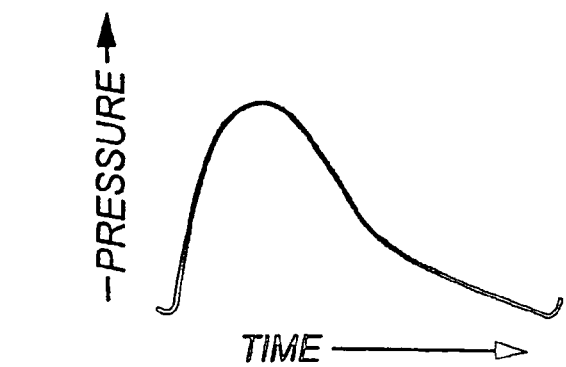
FIG. 3c shows the pressure waveform in a peripheral artery associated with vasodilation.

Harmonic analysis of the pressure waveforms is then performed and the harmonic moduli compared. FIG. 3a shows the pressure wave in a young man under normal conditions, FIG. 3b shows the pressure wave after blood loss associated with tachycardia, and 3c shows the same waves in the hypotensive state with system or organ failure.

Figure 4A:
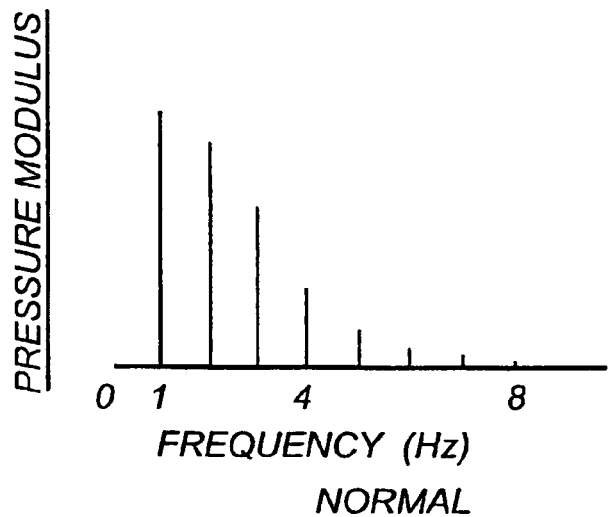
FIG. 4a shows the harmonic moduli of the pressure waveform of FIG. 3a, FIG. 4b shows the harmonic moduli of the pressure waveform of FIG. 3b.
Figure 4B:
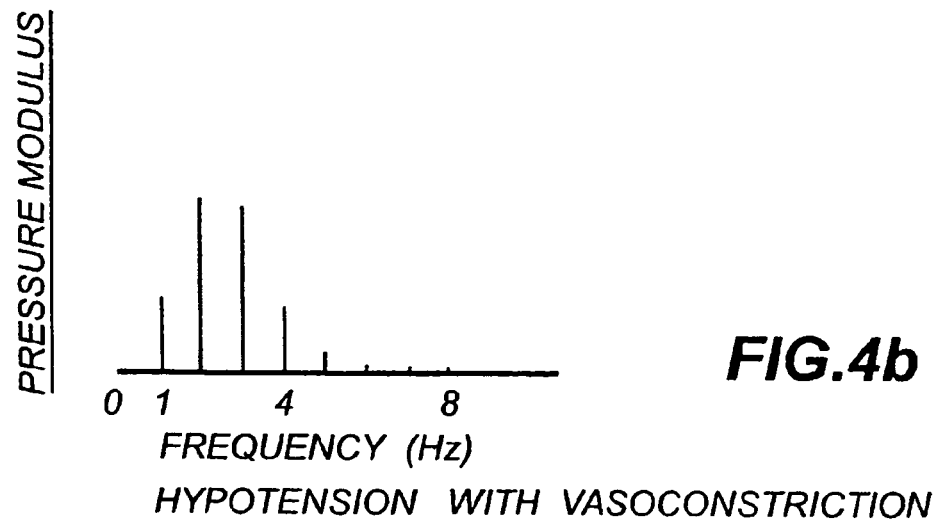
FIG. 4c shows the harmonic moduli of the pressure waveform of FIG. 3c.
Figure 4C:
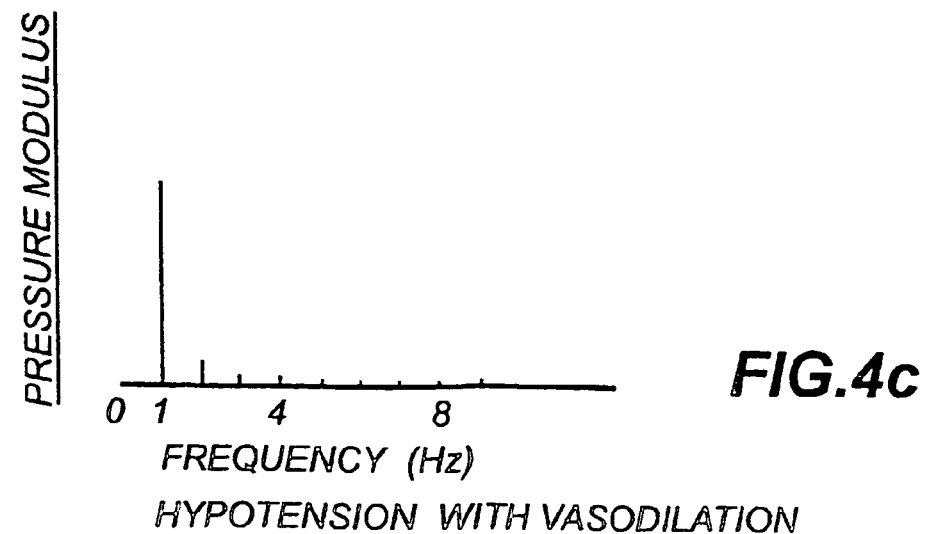

FIGS. 4a to 4c show harmonic moduli under these three different conditions together with differences in amplitude of primary and secondary pressure waveforms.

Figure 5:
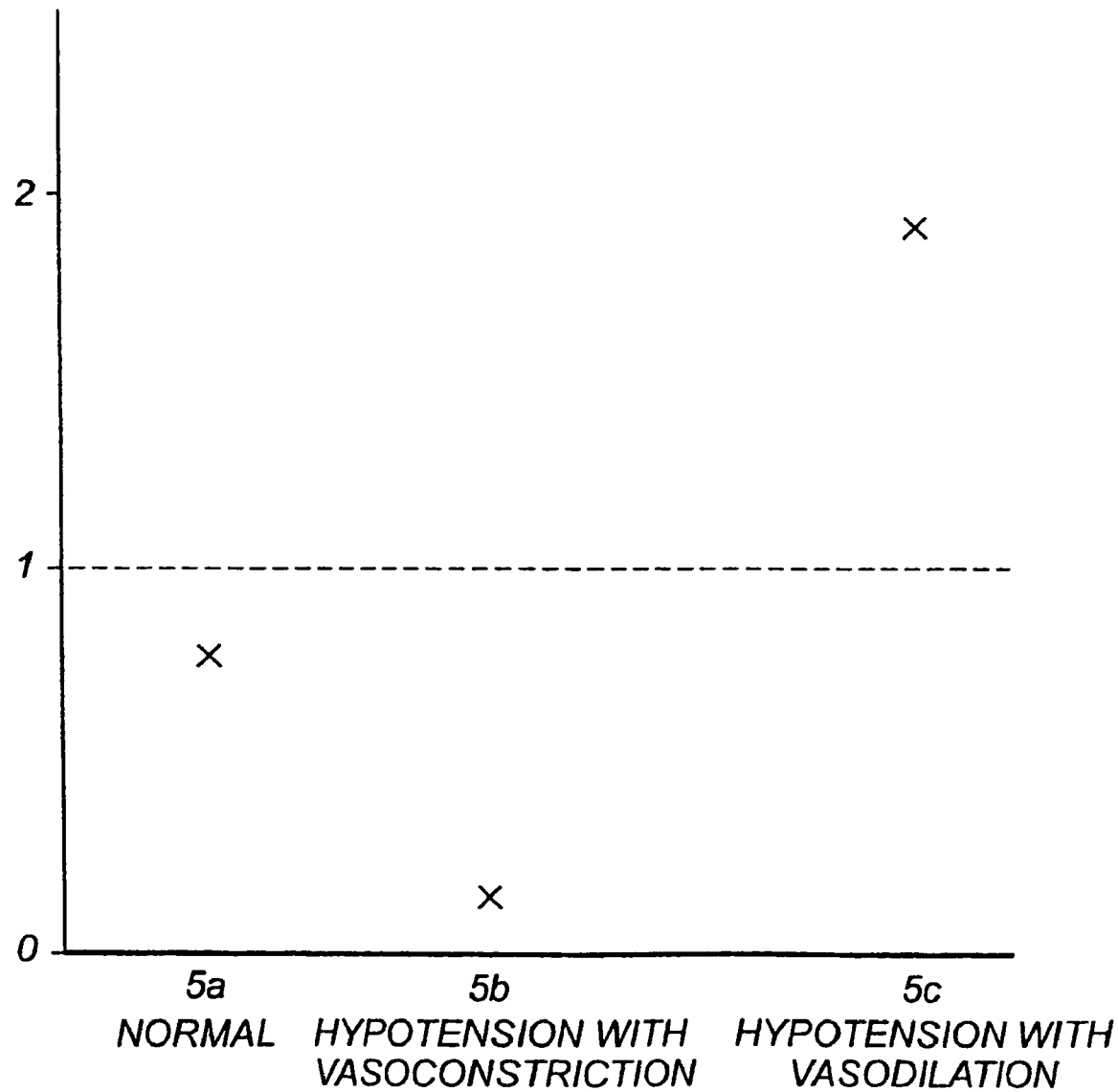
FIG. 5a shows the ratio of pressure harmonies of the pressure moduli of FIG. 4a, FIG. 5b shows the ratio of pressure harmonies of the pressure moduli of FIG. 4b.
FIG. 5c shows the ratio of pressure harmonies of the pressure moduli of FIG. 4c.

FIGS. 5a to 5c show the ratio of harmonic moduli (H) of FIGS. 4a to 4c as follows:

FIG. 5a—the first harmonic is greater than the subsequent harmonics and the ratio $$\frac{H1}{\Sigma(H2 \text{ to } H5)} \text{ approximates } 0.5 - 1.0$$

FIG. 5b—the higher harmonics are dominant and the ratio $$\frac{H1}{\Sigma(H2 \text{ to } H5)} \text{ is much less than } 0.5$$

FIG. 5c—the first harmonic is completely dominant and the ratio:

$$\frac{H1}{\Sigma(H2 \text{ to } H5)} \text{ is much greater than } 1.0$$

FIGS. 5a to 5c show how the hypotensive state due to blood or fluid loss or acute heart failure or tamponade can be separated from the hypotensive state caused by organ failure through comparison of the harmonic components of the waves. Under normal conditions, the first harmonic component is dominant over other harmonics, but higher harmonics are well represented in the pulse waveform—see FIG. 5a. In the second condition (vasoconstriction) the second and higher harmonics are dominant over the first—see FIG. 5b, whereas in the last condition (organ failure with vasodilation) the first harmonic at heart rate frequency is utterly dominant over all others—see FIG. 5c.

Various modifications may be made in details of the method without departing from the scope and ambit of the invention.

The invention claimed is:

1. A method for providing a diagnosis as to whether hypotension in a patient is due to vasodilation or is associated with compensatory vasoconstriction, said method comprising the steps of:
   (i) measuring the arterial waveforms from a periphery artery,
   (ii) performing an harmonic analysis on said measured waveforms and comparing the moduli of the harmonic components,
   (iii) diagnosing the cause of hypotension as being vasodilation if the modulus of the second harmonic is less than the modulus of the first harmonic, and
   (iv) diagnosing hypotension as being associated with vasoconstriction if the modulus of the first harmonic is less than the modulus of the second harmonic.

2. A method according to claim 1, part (iii), comprising the further steps of assessing the patient's heart rate and determining the presence of absence of significant arrhythmia, and wherein, in the absence of significant arrhythmia and where the heart rate is less than 120 beats per minute, diagnosing the cause of hypotension as being vasodilation.

3. A method according to claim 1, part (iv) and wherein said harmonic analysis includes the step of determining the ratio of the first harmonic to the sum of the subsequent harmonics, the further step of diagnosing hypotension as being associated with vasoconstriction, if the ratio is much less than 0.5, and diagnosing the cause of hypotension as being vasodilation if the ratio is much greater than 1.0.

* * * * *